(12) United States Patent
Nishizawa et al.

(10) Patent No.: US 6,594,336 B2
(45) Date of Patent: Jul. 15, 2003

(54) ABSORPTION DOSE MEASURING APPARATUS FOR INTENSITY MODULATED RADIO THERAPY

(75) Inventors: Hiroshi Nishizawa, Tokyo (JP); Kiyoshi Yoda, Tokyo (JP); Keiichi Matsuo, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/956,913

(22) Filed: Sep. 21, 2001

(65) Prior Publication Data

US 2002/0131552 A1 Sep. 19, 2002

(30) Foreign Application Priority Data

Mar. 14, 2001 (JP) ........................ 2001-072172

(51) Int. Cl.$^7$ ................................ A61N 5/00
(52) U.S. Cl. ........................... 378/65; 250/367
(58) Field of Search .................. 378/65, 207, 18; 250/368, 367, 580, 250, 370.08

(56) References Cited

U.S. PATENT DOCUMENTS

| | | | |
|---|---|---|---|
| 5,391,879 A | * | 2/1995 | Tran et al. ............... 250/367 |
| 5,430,308 A | * | 7/1995 | Feichtner et al. ......... 250/580 |
| 5,856,673 A | | 1/1999 | Ikegami et al. |
| 5,905,263 A | * | 5/1999 | Nishizawa et al. ......... 250/368 |
| 6,066,851 A | * | 5/2000 | Madono et al. ............ 250/367 |
| 6,364,529 B1 | * | 4/2002 | Dawson ..................... 378/207 |

FOREIGN PATENT DOCUMENTS

JP 10153662 * 6/1998 ............. G01T/1/20

OTHER PUBLICATIONS

"Dosimetry IMRT/3D QA Phantom", *MED-TEC*, www.medtec.com.

\* cited by examiner

*Primary Examiner*—Drew A. Dunn
*Assistant Examiner*—Irakli Kiknadze
(74) *Attorney, Agent, or Firm*—Leydig, Voit & Mayer, Ltd.

(57) ABSTRACT

An intensity modulated radio therapy (IMRT) dosimeter measuring a three-dimensional absorption dose distribution in a transparent plastic phantom readily and accurately. In the IMRT dosimeter, radiation beams are directed to a phantom assembly having a scintillation fiber block sandwiched between two blocks of the phantom. As an intensity of light proportional to the radiation beam is emitted from one side of the scintillation fiber block, its profile is measured by an image sensor. Then, the three-dimensional absorption dose distribution is obtained from the light intensity distribution data. By summing the three-dimensional absorption dose distribution data measured with the radiation beam at different angles, an integrated three-dimensional absorption dose distribution in the phantom can be calculated readily and accurately.

10 Claims, 5 Drawing Sheets

ABSORPTION DOSE MEASURING APPARATUS FOR INTENSITY MODULATED RADIO THERAPY

This application is based on the application No. 2001-072172 filed in Japan, the contents of which are hereby incorporated by reference.

BACKGROUND OF THE INVENTION

1. Field of the Invention

The present invention relates to an absorption dose measuring apparatus for intensity modulated radio therapy (referred to as "IMRT" hereinafter), which is used for measuring or evaluating an integrated three-dimensional absorption dose distribution of an X-ray or a particle beam such as an electron beam in a phantom, in the IMRT process for treating cancers.

2. Description of the Prior Art

IMRT is well known as one of radiation therapy processes. In the IMRT, because a radiation beam is applied to a patient while variously changing the shape of the radiation field of the beam and further variously changing the incident direction of the radiation beam, the integrated absorption dose of the radiation may be set so as to match the shape of the affected part to be treated. Accordingly, the radiation therapy process can be effectively carried out with the radiation accurately focused onto the affected part to be treated.

When the IMRT described above is carried out, a treatment plan is made at first. In the treatment plan, there may be set a condition for accurately applying the radiation onto the affected part to be treated, with a predetermined absorption dose distribution of the radiation. The treatment plan must be then examined or verified through experiments whether it is appropriate to the patient. For the verification, in general, an absorption dose measuring apparatus for IMRT (referred to "IMRT dosimeter" hereinafter) is used.

Hereinafter, there will be described a process for measuring an absorption dose distribution in a conventional IMRT dosimeter.

Figure 6:
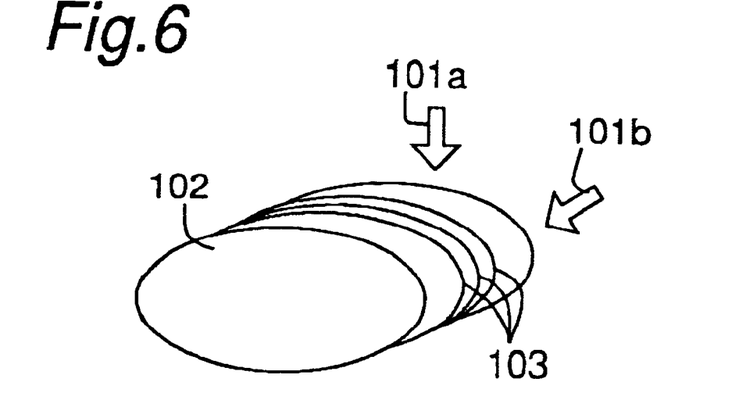
FIG. 6 is a perspective view of a schematic arrangement of a main part of a conventional IMRT dosimeter.

FIG. 6 illustrates a process for measuring an absorption dose distribution in a conventional typical IMRT dosimeter. As shown in FIG. 6, the conventional IMRT dosimeter has a construction that a plurality of X-ray films 103 are interposed at a plurality of positions in a phantom 102 made of a plastic.

In the conventional IMRT dosimeter having the above-mentioned construction, radiation beams 110a and 101b such as X-rays, particle beams such as electron beams or the like are applied to the phantom 102. In consequence, each of the X-ray films 103 interposed in the phantom 102 is exposed (sensitized) due to interactions with the radiation beams. Then, there may be obtained a two-dimensional absorption dose distribution at each of the positions corresponding to the X-ray films 103 by measuring the distribution pattern of darkening degree in the X-ray film 103. Thus, on the basis of the two-dimensional absorption dose distributions of all of the X-ray films 103, a three-dimensional absorption dose distribution in the phantom 102 may be obtained.

In the Japanese Laid-open Patent Publication 9-230053, 10-153662 or 10-153663, there is disclosed a depth dose measuring apparatus which can measure an absorption dose distribution in a phantom in a short duration of time without using X-ray films.

Figure 7:
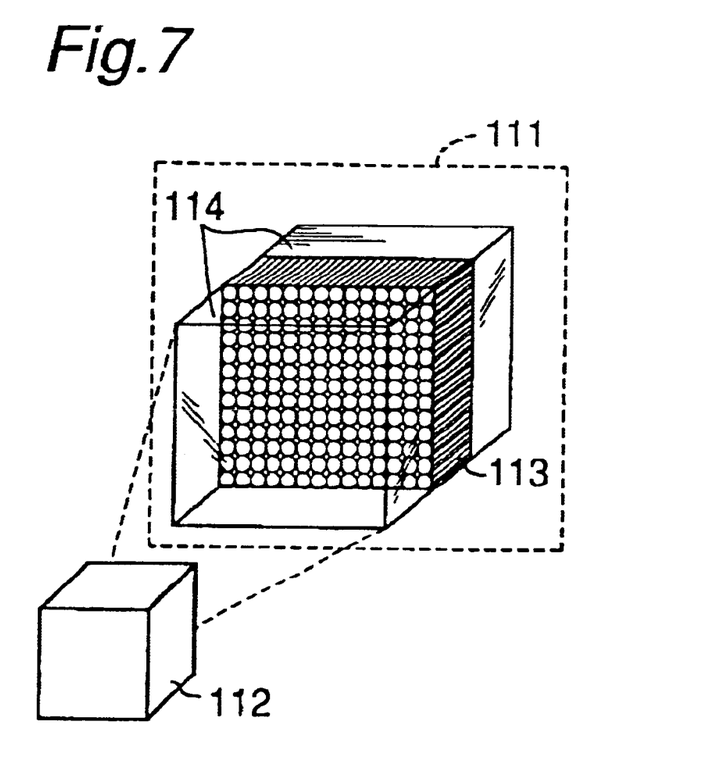
FIG. 7 is a perspective view of a schematic arrangement of a main part of a conventional depth dose measuring apparatus.

FIG. 7 illustrates a schematic arrangement of a depth dose measuring apparatus, disclosed in the above-mentioned Publication 10-153663, for inspection and verification of a radiation emitter for cancer treatment. As shown in FIG. 7, in the depth dose measuring apparatus, a detecting unit 111 is composed of a plastic-made scintillation fiber block 113 substantially equivalent to the human organism and transparent-plastic blocks 114 sandwiching the fiber block 113. Also, provided is an image sensor 112 for measuring a light intensity distribution on one end of the scintillation fiber block 113.

In the depth dose measuring apparatus, the radiation beam is applied onto the upper surface of the detecting unit 111 in the direction perpendicular to the upper surface from above. Because the detecting unit 111 is substantially equivalent to the human organism, its properties for absorbing the radiation are substantially equal to those of the human organism. Therefore, it can correctly measure the absorption dose distribution. In this case, if the detecting unit 111 and the image measuring device 112 are rotated or linearly moved as one body, a three-dimensional absorption dose distribution in the detecting unit 111 may be measured using a steady radiation beam emitted from a radiation emitter.

However, the conventional IMRT dosimeter using X-ray films, for example shown in FIG. 6, may fail to measure the absorption dose distribution at a desired level of accuracy, because the X-ray film is significantly different in absorbing radiation from the human organism. Also, the X-ray film may vary in output depending on production lot or the conditions of development, even if the absorption dose is uniform. Accordingly, the result of the measurement will hardly be consistent in accuracy. The steps of developing the X-ray film and measuring a pattern of the darkening are time and labor intensive.

On the other hand, in the conventional depth dose measuring apparatus, for example shown in FIG. 7, there exists such a problem that it is applicable to the IMRT with much difficulty, even though it is generally capable of measuring the absorption dose distribution accurately and readily. That is, because the IMRT generally measures or evaluates the integrated absorption dose while variously changing the shape of the radiation field and the incident direction of the radiation beams, the above-mentioned conventional depth dose measuring apparatus, which is to use only a steady radiation beam, may hardly provide appropriate measurement or evaluation of the integrated absorption dose distribution for the IMRT process.

SUMMARY OF THE INVENTION

The present invention has been achieved to solve the conventional problems described above, and has an object to provide an IMRT dosimeter which can accurately measure or evaluate a three-dimensional absorption dose distribution in a phantom in a short duration of time for the IMRT process.

According to a first aspect of the present invention, which has been achieved to solve the above-mentioned problems, there is provided an IMRT dosimeter (i.e. absorption dose measuring apparatus for IMRT) which measures (or evaluates) a absorption dose distribution in a phantom for the IMRT, including (i) a detecting section composed of a plastic scintillator and arranged so that its strike is vertical to an incident direction of a radiation beam, (ii) a phantom composed of a transparent plastic and formed (or disposed) to sandwich the detecting section from both sides along a direction parallel with the strike of the plastic scintillator, (iii) an image measuring device for measuring a distribution of intensity of light emitted from one side of the detecting section along the direction parallel with the strike of the plastic scintillator, (iv) an assembly driver for moving an assembly including the detecting section, the phantom and the image measuring device in the direction parallel with the strike of the plastic scintillator, or for rotating the assembly about a rotation axis which extends vertically across a center of the detecting section, and (v) a data processor for processing a data measured by the image measuring device. Hereupon, (vi) the data processor picks (or gathers) a three-dimensional absorption dose distribution data in the phantom when the assembly driver moves the assembly in the direction parallel with the strike of the plastic scintillator or rotates the assembly about the rotation axis, at each of plural radiation beam applications each of which is performed under a predetermined condition. Further, (vii) the data processor obtains an integrated three-dimensional absorption dose distribution in the phantom by summing (or combining, or synthesizing) the three-dimensional absorption dose distribution data for each of the radiation beam applications.

In the IMRT dosimeter of the first aspect of the present invention, the data processor, for example composed of a computer or the like, picks (or gathers) the three-dimensional absorption dose distribution data in the phantom in each of the plural applications of the radiation beams. Further, the data processor obtains the integrated three-dimensional absorption dose distribution for the IMRT by summing the three-dimensional absorption dose distribution for the plural applications of the radiation beams. Because the integrated three-dimensional absorption dose distribution is obtained by the data processing using the computer or the like, the absorption dose distribution may be measured with a higher accuracy in a short period.

In an IMRT dosimeter of a second aspect of the present invention, the IMRT dosimeter of the first aspect is modified so that the detecting section is composed of a plastic scintillator which is formed by bundling plastic scintillation fibers in a block shape.

According to the IMRT dosimeter of the second aspect of the present invention, at first, there may be obtained advantages similar to those of the IMRT dosimeter of the first aspect of the present invention. In addition, because the plastic scintillator formed by bundling the plastic scintillation fibers in the block shape is used, the light produced in the detecting section by the radiation beam can be certainly guided by the scintillation fibers to reach the end surface of the detecting section. In consequence, the distribution of the light intensity in the detecting section can accurately appear at the end surface of the detecting section so that the accuracy of measuring the integrated three-dimensional absorption dose distribution may be improved.

In an IMRT dosimeter of a third aspect of the present invention, the IMRT dosimeter of the first aspect is modified so that the detecting section is composed of a plastic scintillator of a thin plate shape (or form).

According to the IMRT dosimeter of the third aspect of the present invention, at first, there may be obtained advantages similar to those of the IMRT dosimeter of the first aspect of the present invention. In addition, because the detecting section is formed of the plastic scintillator of the thin plate shape, diffusion of the light produced in the detecting section by the radiation beam is reduced so that the accuracy of measuring the integrated three-dimensional absorption dose distribution may be improved. Moreover, the cost for producing the detecting section or the IMRT dosimeter may be reduced.

In an IMRT dosimeter of a fourth aspect of the present invention, the IMRT dosimeter of the second or third aspect is modified so that a cross section of an assembly composed of the phantom and the detecting section has a shape similar to a shape of a cross section of a human body.

According to the IMRT dosimeter of the fourth aspect of the present invention, at first, there may be obtained advantages similar to those of the IMRT dosimeter of the second or third aspect of the present invention. In addition, because the shape of the cross section of the assembly composed of the phantom and the detecting section is similar to that of the human body, the absorption dose distribution in the human body for the IMRT may be correctly evaluated, before the patient is actually exposed to the radiation beam in accordance with the treatment plan.

In an IMRT dosimeter of a fifth aspect of the present invention, the IMRT dosimeter of any one of the first to fourth aspects is modified so that (i) the incident direction of the radiation beam is fixed to a direction perpendicular to an upper surface of an (or the) assembly composed of the phantom and the detecting section when the integrated three-dimensional absorption dose distribution is measured, (ii) while the integrated three-dimensional absorption dose distribution in the phantom is obtained by summing (or combining, or synthesizing) the three-dimensional absorption dose distribution data in consideration of an incident angle of a radiation which has been planed for the IMRT.

According to the IMRT dosimeter of the fifth aspect of the present invention, at first, there may be obtained advantages similar to those of the IMRT dosimeter of any one of the first to fourth aspects of the present invention. In addition, the three-dimensional absorption dose distribution data can be measured without changing the incident direction of the radiation beam toward the phantom and the detecting section, when the radiation beams are applied in various incident directions. Accordingly, the integrated three-dimensional absorption dose distribution for the IMRT can be accurately measured in a short period while simplifying the construction of the radiation generator or the IMRT dosimeter.

BRIEF DESCRIPTION OF THE DRAWINGS

Various characteristics and advantages of the present invention will become clear from the following description taken in conjunction with the preferred embodiments with reference to the accompanying drawings throughout which like parts are designated by like reference numerals, in which.

DETAILED DESCRIPTION OF THE PREFERRED EMBODIMENTS

Hereinafter, some preferred embodiments of the present invention will be described in more detail.

(Embodiment 1)

Figure 1:
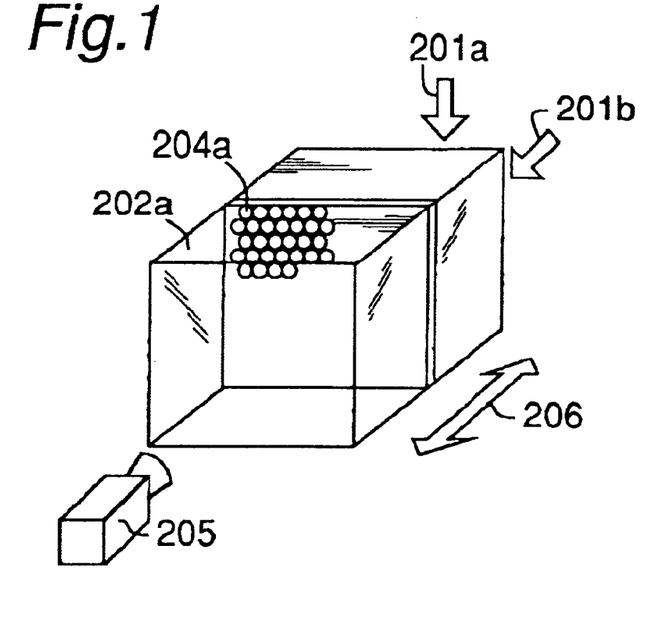
FIG. 1 is a perspective view of a schematic arrangement of a main part of an IMRT dosimeter according to Embodiment 1 of the present invention.

Hereinafter, Embodiment 1 of the present invention will be explained. FIG. 1 illustrates a schematic arrangement of a main part of an IMRT dosimeter according to Embodiment 1 of the present invention. As shown in FIG. 1, in the IMRT dosimeter, radiation beams 201$a$ and 201$b$ such as X-rays, particle beams such as electron beams, or the like are applied to a combination or assembly of a rectangular parallelepiped or cubic shape (referred to "phantom assembly" hereinafter) including a phantom 202$a$ and a scintillation fiber block 204$a$ (i.e. detecting section). An intensity distribution of light emitted from one end surface of the scintillation fiber block 204$a$ is measured by an image sensor 205 (image measuring device) such as a CCD camera.

Denoted by the arrow 206 is the directions along which the assembly including the phantom 202$a$, the scintillation fiber block 204$a$ and the image sensor 205 (referred to "movable module" hereinafter) is moved during the measurement of the absorption dose distribution. Hereinafter, for convenience sake, it is assumed that the "front" is at the side of the image sensor 205 in the direction that the phantom 202$a$, the scintillation fiber block 204$a$ and the image sensor 205 are aligned in a row, while the "rear" is at the opposite side.

The phantom 202$a$ includes a pair of front and rear transparent plastic blocks. The scintillation fiber block 204$a$ consists mainly of a multiplicity of scintillation fibers bundled in a block, and sandwiched between the two, front and rear, plastic blocks of the phantom 202$a$. The radiation absorption property of the scintillation fiber block 204$a$ is substantially equal to that of the phantom 202$a$. The phantom 202$a$ and the scintillation fiber block 204$a$ are substantially equivalent in the radiation absorption properties to the human organism.

The longitudinal distance (length) of the phantom 202$a$ or the phantom assembly, namely the distance (length) extending along the direction of movement denoted by the arrow 206, is favorably determined to such a length that the radiation beams 201$a$ and 201$b$ are applied onto the phantom assembly with the movable module sited in any position during the measurement of the absorption dose distribution. Meanwhile, to the phantom assembly, the radiation beams 201$a$ and 201$b$ are incident at a right angle to the direction of the strike of the scintillation fiber block 204$a$ (i.e. along the axis of the scintillation fiber or the longitudinal direction of the block). That is, the scintillation fiber block 204$a$ is disposed so that the direction of its strike extends vertically to each of the radiation beams 201$a$ and 201$b$.

An action or function of the IMRT dosimeter shown in FIG. 1 will now be described. At first, the radiation beam 201$a$ is directed from above to the phantom assembly. This allows each scintillation fiber in the scintillation fiber block 204$a$ between the front and rear blocks of the phantom 202$a$ to emit a light of an intensity proportional to the absorption dose. A distribution of the light intensity on the front surface of the scintillation fiber block 204$a$ is then measured by the image sensor 205. It is now obtained a two-dimensional absorption dose distribution at a position where the scintillation fiber block 204$a$ exists.

Further, as the movable module has been moved by a predetermined distance in one of the two longitudinal directions (i.e. along the axis) of the scintillation fiber in the scintillation fiber block 204$a$ as denoted by the arrow 206, the measurement of the two-dimensional absorption dose distribution at the position, where the scintillation fiber block 204$a$ exists, is measured. By repeating this action, plural two-dimensional absorption dose distributions arranged at intervals of predetermined distances are successively obtained, and then a three-dimensional absorption dose distribution in the phantom 202$a$ can be obtained on the basis of the two-dimensional absorption dose distribution data. Alternatively, the movable module may be rotated about a rotation axis extending vertically across the center of the scintillation fiber block 204$a$ to obtain the three-dimensional absorption dose distribution, instead of being moved linearly.

In the IMRT, generally, the radiation beam is repeatedly applied to an affected part of the patient to be treated while variously changing the shape of the radiation field of the beam and further variously changing the incident direction of the radiation beam, namely variously changing the conditions of the radiation beam. In consequence, the IMRT dosimeter measures the three-dimensional absorption dose distribution in the phantom 202$a$ in various radiation conditions (the shape of the radiation field and the incident direction of the radiation). After the measurement has been completed for all of the radiation conditions, the IMRT dosimeter sums (or combines, or synthesizes) the absorption dose at each position to calculate the integrated three-dimensional absorption dose distribution in the phantom for the IMRT accurately and readily. Then, the integrated three-dimensional absorption dose distribution, which has been obtained as described above, is compared with a simulated value of the absorption dose calculated under the same conditions by the treatment plan (treatment planning apparatus) to examine or verify whether the treatment plan is appropriate.

(Embodiment 2)

Hereinafter, Embodiment 2 of the present invention will be described with reference to FIG. 2. However, the IMRT dosimeter of Embodiment 2 is mostly identical in the arrangement to that of Embodiment 1 described in conjunction with FIG. 1. Therefore, in order to avoid duplicated description, the description of common elements between Embodiment 1 and Embodiment 2 will be omitted but not specific elements which are not provided in Embodiment 1.

Figure 2:
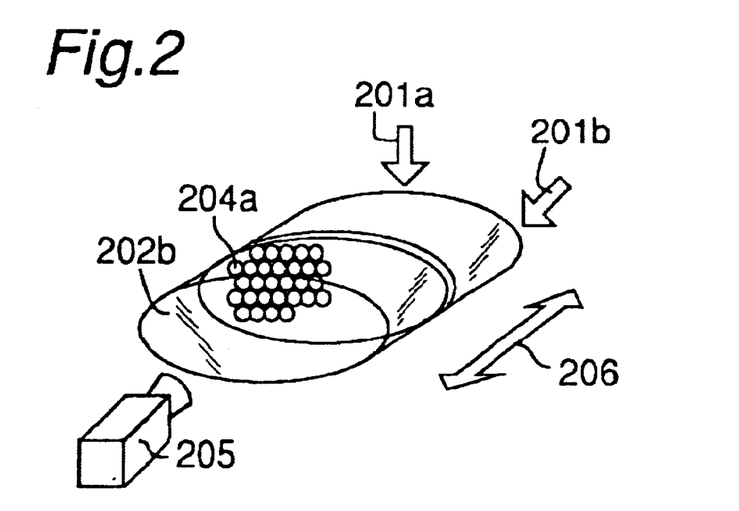
FIG. 2 is a perspective view of a schematic arrangement of a main part of an IMRT dosimeter according to Embodiment 2 of the present invention.

FIG. 2 illustrates a schematic arrangement of a main part of the IMRT dosimeter according to Embodiment 2 of the present invention. In FIG. 2, like components are denoted by like numerals as those of Embodiment 1, and will be explained in no more detail. As described previously, the phantom assembly in the IMRT dosimeter of Embodiment 1 includes the phantom 202$a$ and the fiber block 204$a$, and is arranged of a rectangular parallelepiped or cubic shape. On the other hand, the IMRT dosimeter of Embodiment 2 has a phantom assembly composed of a phantom 202$b$ and a fiber block 204$a$ and arranged of a configuration similar to the shape of a human body. This is a single, substantial factor of difference between Embodiment 1 and Embodiment 2.

Because the phantom assembly of the IMRT dosimeter of Embodiment 2 is similar in the shape to the human body as described above, the absorption dose distribution in the phantom for the IMRT can be measured and evaluated accurately and readily before the radiation beam is actually applied to the patient. Thus, the absorption dose distribution measured as described above is compared with a simulated value of the absorption dose calculated by a treatment plan to judge or evaluate whether the treatment plan is appropriate or not.

(Embodiment 3)

Hereinafter, Embodiment 3 of the present invention will be described with reference to FIG. 3. However, the IMRT dosimeter of Embodiment 3 is mostly identical in the arrangement to that of Embodiment 1 described in conjunction with FIG. 1. Therefore, in order to avoid duplicated description, the description of common elements between Embodiment 1 and Embodiment 3 will be omitted but not specific elements which are not provided in Embodiment 1.

Figure 3:
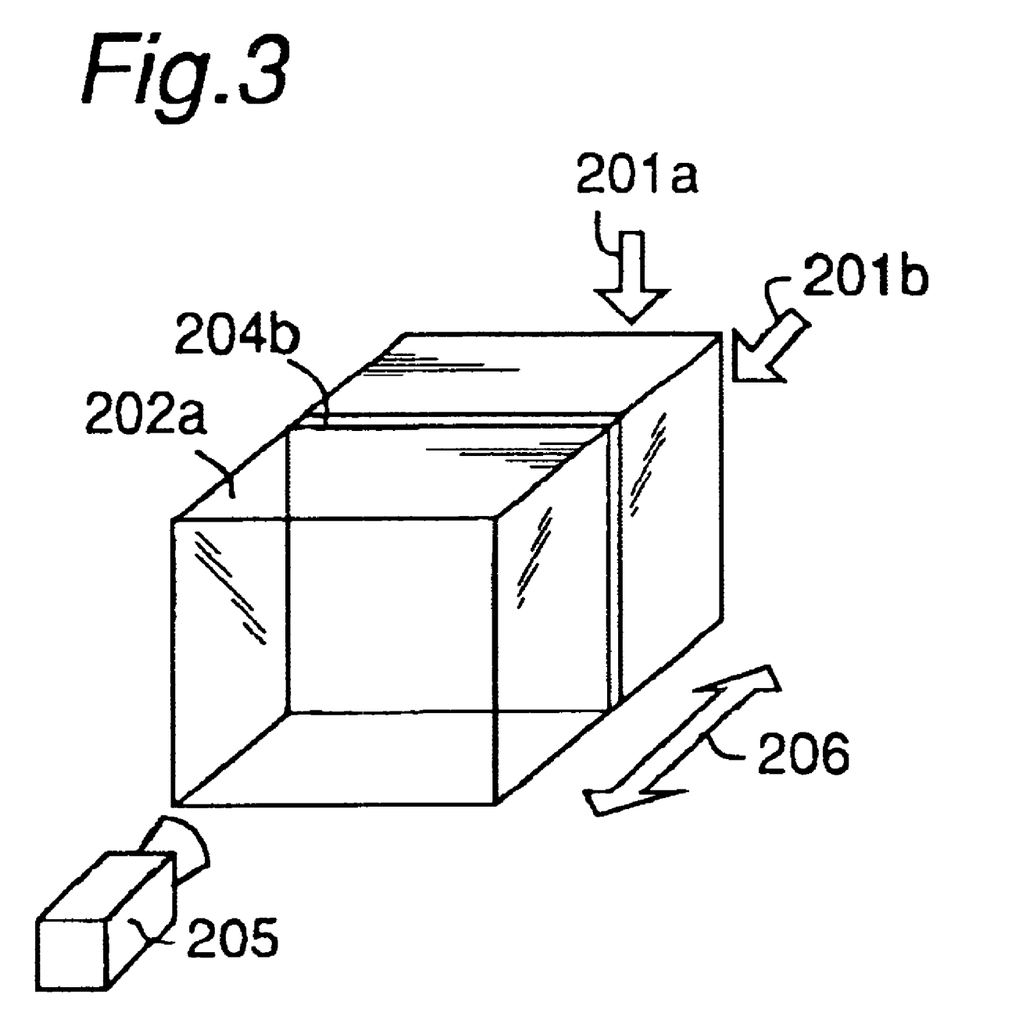
FIG. 3 is a perspective view of a schematic arrangement of a main part of an IMRT dosimeter according to Embodiment 3 of the present invention.

FIG. 3 illustrates a schematic arrangement of the IMRT dosimeter according to Embodiment 3 of the present invention. In FIG. 3, like components are denoted by like numerals as those of Embodiment 1, and will be explained in no more detail. As described previously, the scintillation fiber block 204a (detecting section) for detecting the absorption dose in the IMRT dosimeter of Embodiment 1 includes a multiplicity of the scintillation fibers, and is sandwiched between the two, front and rear, blocks of the phantom 202a.

On the other hand, the IMRT dosimeter of Embodiment 3 has a plastic scintillator 204b (detecting section) of a thin plate shape for detecting the absorption dose, sandwiched between the two, front and rear, blocks of the phantom 202a. This is a single, substantial difference between Embodiment 1 and Embodiment 3. In this case, the strike of the plastic scintillator 204b is identical to the direction of its thickness (forward and backward).

Because the plastic scintillator 204b of the IMRT dosimeter of Embodiment 3 is thin, it permits diffusion of light caused by the incident beam of radiation to be reduced thus improving the positional resolution. Also, because the plate shape of the plastic scintillator 204b can be easily made, its cost or the cost of the IMRT dosimeter can be lowered.

The phantom assembly composed of the phantom 202a and the plastic scintillator 204b may be formed of a configuration similar to the shape of a human body, like that of Embodiment 2.

(Embodiment 4)

Hereinafter, Embodiment 4 of the present invention will be described with reference to FIGS. 4 and 5.

Figure 4:
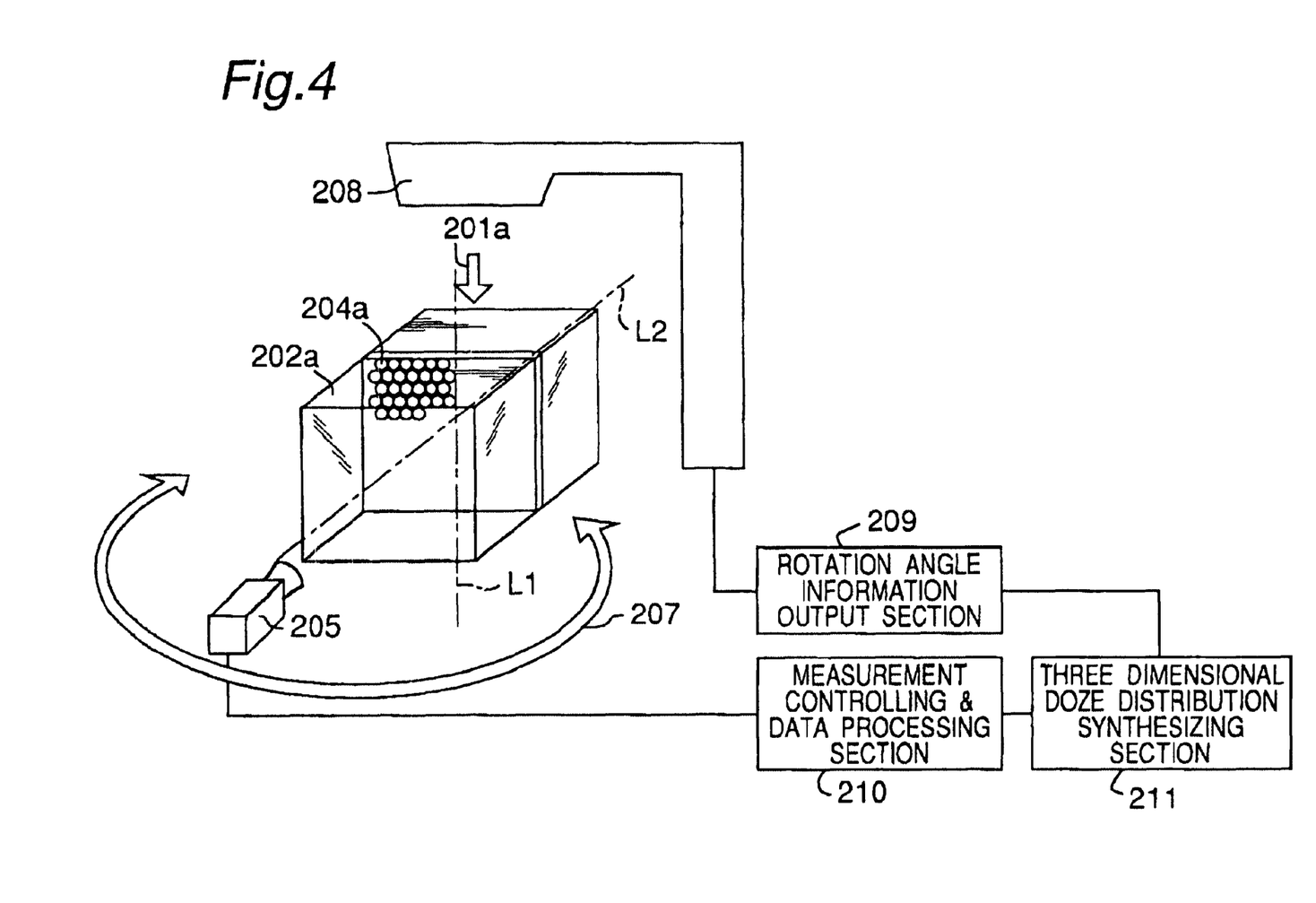
FIG. 4 is a perspective view of a schematic arrangement of an IMRT dosimeter according to Embodiment 4 of the present invention.

FIG. 4 illustrates a schematic arrangement of an IMRT dosimeter according to Embodiment 4 of the present invention. As shown in FIG. 4, in the IMRT dosimeter, a radiation beam 201a such as an X-ray, a particle beam such as an electron beam, or the like, which is emitted from a radiation generator 208, is applied to a phantom assembly of a rectangular parallelepiped or cubic shape including a phantom 202a and a scintillation fiber block 204a. Then, an intensity distribution of light emitted from the front surface of the scintillation fiber block 204a is measured by an image sensor 205 such as a CCD camera. The phantom 202a, the scintillator 204a and the image measuring device 205 are identical in the construction and function to those of Embodiment 1.

The phantom 202a, the scintillation fiber block 204a and the image measuring device 205 are assembled to a movable module which can turn about the vertical center axis L1 extending vertically across the center of the phantom assembly in the directions denoted by the arrow 207 during the measurement of the absorption dose distribution.

The IMRT dosimeter includes a rotation angle information output section (or means) 209 for outputting information about the relative rotation angle of the radiation generator 208 (corresponding to the incident angle of the radiation beam) around the horizontal center axis L2 of the phantom assembly. Further, the IMRT dosimeter includes a measurement controlling & data processing section (or means) 210 for controlling the measurement of the dose distribution and processing an image data generated by the image sensor 205, and a three-dimensional dose distribution synthesizing (or combining) section (or means) 211 for composing a three-dimensional absorption dose distribution on the basis of the image data processed by the measurement controlling & data processing section 210.

Hereinafter, an action or function of the IMRT dosimeter of Embodiment 4 will be described. At first, the radiation beam 201a emitted from the radiation generator 208 is directed from above to the phantom assembly which includes the phantom 202a and the scintillation fiber block 204a. This allows each scintillation fiber in the scintillation fiber block 204a between the front and rear blocks of the phantom 202a to emit a light with an intensity proportional to its absorption dose. Then, the distribution of the light intensity on the front surface of the scintillation fiber block 204a is measured by the image sensor 205. Thus, it is immediately measured a two-dimensional absorption dose distribution at the position where the scintillation fiber block 204a exists.

After the movable module is rotated by a predetermined angle about the vertical center axis L1 of the phantom assembly in one of the directions denoted by the arrow 207, another two-dimensional absorption dose distribution is measured at the position where the scintillation fiber block 204a exists, by the same manner as descried above. The above-mentioned operations are repeated. As a result, a series of the two-dimensional absorption dose distributions at intervals of the predetermined angles are successively obtained. Then, a three-dimensional absorption dose distribution data in the phantom 202a may be obtained on the basis of the two-dimensional absorption dose distribution data.

In common practice of any previous IMRT dosimeter, the radiation beam is applied to the patient whose position is fixed while variously changing the shape of the radiation field and the incident direction of the radiation beam. However, the IMRT dosimeter of Embodiment 4 allows the phantom assembly to receive the radiation beam 201a vertically at its upper surface for the measurement of the absorption dose distribution.

For carrying out the actual IMRT treatment, the radiation generator is turned in accordance with a treatment plan determined by a treatment planning apparatus to irradiate the patient (or the phantom) from various directions. In the IMRT dosimeter, the data about the incident angle of the radiation beam is output from the rotation angle information output section 209, and then received by the three-dimensional dose distribution synthesizing section 211. This simulates that the radiation generator and the IMRT dosimeter are rotated about the horizontal center axis L2. As a result, a three-dimensional absorption dose distribution at different incident angles is calculated by the three-dimensional dose distribution synthesizing section 211.

Meanwhile, the data of the absorption dose distribution measured by the image sensor 205 is processed by the measurement controlling & data processing section 210. The data output from the measurement controlling & data processing section 210 and the data output from the rotation angle information output section 209 are transmitted to the three-dimensional dose distribution synthesizing section 211. Thus, the data are processed by the three-dimensional dose distribution synthesizing section 211. In consequence, the three-dimensional absorption dose distribution is produced as same as the case that the radiation beam is applied in various directions by rotating the radiation generator 208. The resultant absorption dose distribution data is then compared with the simulated dose distribution calculated under the same conditions for the treatment plan in the IMRT to verify or evaluate the propriety of the treatment plan.

It is common that the duration of applying the radiation in the actual IMRT treatment is not more than several seconds at each condition (the shape of the radiation field and the incident direction of the beam). However, a full turn of the movable module in the IMRT dosimeter may take several ten seconds to several minutes for measuring one three-dimensional absorption dose distribution when the three-dimensional dose distribution is measured using the IMRT dosimeter. Accordingly, when the three-dimensional absorption dose distribution is measured using the IMRT dosimeter of this embodiment, it can be measured or evaluated at precision by increasing the duration of applying the radiation by a uniform ratio at each of the different radiation-applying conditions. This advantage is feasible in each of Embodiments 1 to 3 where the movable module is arranged for linear movement.

Figure 5:
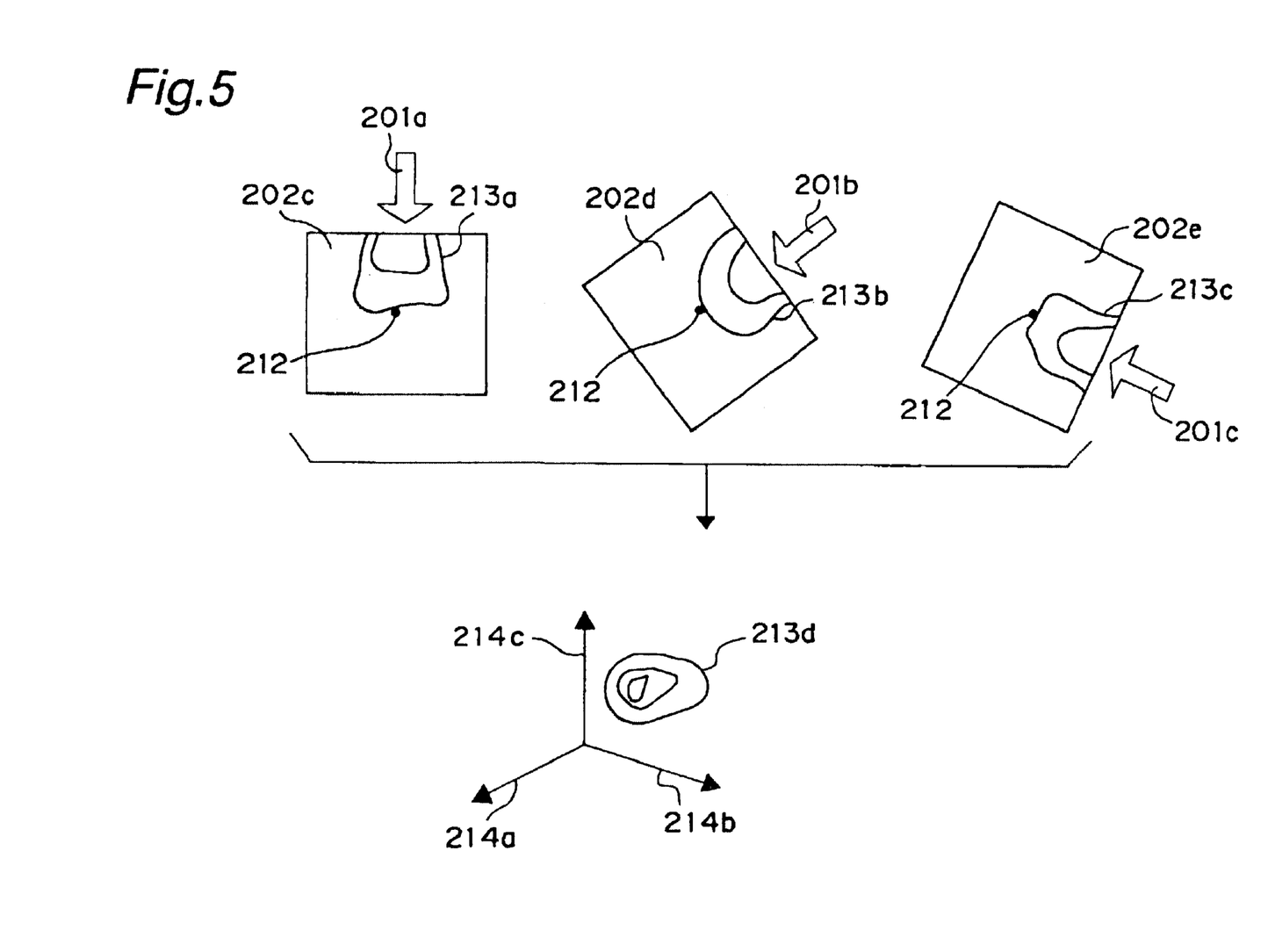
FIG. 5 is a diagram showing a method of calculating a three-dimensional absorption dose distribution by a treatment planning apparatus, according to Embodiment 4 of the present invention.

Thus, the data measured by the IMRT dosimeter is compared with, for example, a reference data determined by simulating the treatment plan as shown in FIG. 5, whereby the propriety of the treatment plan can be verified or evaluated.

Referring to FIG. 5, the radiation beams are denoted by 201a, 201b and 201c. Also, denoted by 202c, 202d and 202e are phantoms at their respective beams. Denoted by 212 is the center of turning of the radiation generator or each of the phantoms 202c, 202d and 202e. Denoted by 213a, 213b, 213c and 213d are the contour lines of simulated dose.

The treatment plan simulates the radiation beams 201a, 201b and 201c with various incident directions. On that occasion, the phantoms 202c, 202d and 202e are also turned to match the incident directions of the radiation beams 201a, 201b and 201c. It should be noted that the radiation beams 201a, 201b and 201c are incident always at a right angle to the upper surface of their respective phantoms 202c, 202d and 202e. By summing (or combining) the absorption dose distributions determined at such different locations by simulating the treatment plan, a calculated three-dimensional absorption dose distribution 213d (the absorption dose distribution measured or calculated in the three-dimensional location) can be obtained. The calculated three-dimensional absorption dose distribution 213d is then compared with the three-dimensional absorption dose distribution measured by the IMRT dosimeter shown in FIG. 4, whereby the propriety of the treatment plan can be verified or evaluated.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. An absorption dose measuring apparatus for intensity modulated radio therapy, which measures an absorption dose distribution in a phantom for the intensity modulated radio therapy, comprising:

a detecting section including a plastic scintillator having a strike perpendicular to an incident direction of a radiation beam;

a transparent plastic phantom sandwiching said detecting section at opposite sides along a direction parallel to said strike of said plastic scintillator;

an image measuring device for measuring a distribution of intensity of light emitted from one side of said detecting section along the direction parallel to said strike of said plastic scintillator;

an assembly driver for one of (i) moving an assembly including said detecting section, said phantom, and said image measuring device, in the direction parallel to said strike of said plastic scintillator, and (ii) rotating said assembly about a rotation axis which extends across a center of said detecting section; and a data processor for processing data measured by said image measuring device, wherein said data processor selects three-dimensional absorption dose distribution data in said phantom when said assembly driver moves said assembly in the direction parallel to said strike of said plastic scintillator or rotates said assembly about said rotation axis, at each of plural radiation beam applications, and produces an integrated three-dimensional absorption dose distribution in said phantom by summing the three-dimensional absorption dose distribution data for each of the radiation beam applications.

2. The absorption dose measuring apparatus according to claim 1, wherein said plastic scintillator includes bundled plastic scintillation fibers in a block.

3. The absorption dose measuring apparatus according to claim 1, wherein said plastic scintillator has a thin plate shape.

4. The absorption dose measuring apparatus according to claim 2, wherein a cross section of a second assembly including said phantom and said detecting section has a shape similar to a cross section of a human body.

5. The absorption dose measuring apparatus according to claim 3, wherein a cross section of a second assembly including said phantom and said detecting section has a shape similar to a cross section of a human body.

6. The absorption dose measuring apparatus according to claim 1, wherein the incident direction of the radiation beam is perpendicular to an upper surface of a second assembly including said phantom and said detecting section when the integrated three-dimensional absorption dose distribution is measured, and the integrated three-dimensional absorption dose distribution in said phantom is obtained by summing the three-dimensional absorption dose distribution data considering incident angle of radiation which has been made planar for the intensity modulated radio therapy.

7. The absorption dose measuring apparatus according to claim 2, wherein the incident direction of the radiation beam is perpendicular to an upper surface of a second assembly including said phantom and said detecting section when the integrated three-dimensional absorption dose distribution is measured, and the integrated three-dimensional absorption dose distribution in said phantom is obtained by summing the three-dimensional absorption dose distribution data considering incident angle of radiation which has been made planar for the intensity modulated radio therapy.

8. The absorption dose measuring apparatus according to claim 3, wherein the incident direction of the radiation beam is perpendicular to an upper surface of a second assembly including said phantom and said detecting section when the integrated three-dimensional absorption dose distribution is measured, and the integrated three-dimensional absorption dose distribution in said phantom is obtained by summing the three-dimensional absorption dose distribution data considering incident angle of radiation which has been made planar for the intensity modulated radio therapy.

9. The absorption dose measuring apparatus according to claim 4, wherein the incident direction of the radiation beam is perpendicular to an upper surface of a second assembly including said phantom and said detecting section when the integrated three-dimensional absorption dose distribution is measured, and the integrated three-dimensional absorption dose distribution in said phantom is obtained by summing the three-dimensional absorption dose distribution data considering incident angle of radiation which has been made planar for the intensity modulated radio therapy.

10. The absorption dose measuring apparatus according to claim 5, wherein the incident direction of the radiation beam is perpendicular to an upper surface of a second assembly including said phantom and said detecting section when the integrated three-dimensional absorption dose distribution is measured, and the integrated three-dimensional absorption dose distribution in said phantom is obtained by summing the three-dimensional absorption dose distribution data considering incident angle of radiation which has been made planar for the intensity modulated radio therapy.

* * * * *